United States Patent
Greene et al.

(10) Patent No.: US 9,914,672 B2
(45) Date of Patent: Mar. 13, 2018

(54) CONVERSION OF ALCOHOLS TO DISTILLATE FUELS

(71) Applicant: Lummus Technology Inc., Bloomfield, NJ (US)

(72) Inventors: Marvin I. Greene, Clifton, NJ (US); Ruozhi Song, Wilmington, DE (US); Arvids Judzis, Jr., Houston, TX (US)

(73) Assignee: Lummus Technology Inc., Bloomfield, NJ (US)

( * ) Notice: Subject to any disclaimer, the term of this patent is extended or adjusted under 35 U.S.C. 154(b) by 659 days.

(21) Appl. No.: 14/052,972

(22) Filed: Oct. 14, 2013

(65) Prior Publication Data

US 2014/0114101 A1     Apr. 24, 2014

Related U.S. Application Data

(60) Provisional application No. 61/716,120, filed on Oct. 19, 2012.

(51) Int. Cl.
*C07C 1/24* (2006.01)
*C07C 2/06* (2006.01)
(Continued)

(52) U.S. Cl.
CPC ............. *C07C 1/24* (2013.01); *C07C 2/06* (2013.01); *C07C 5/13* (2013.01); *C10G 3/42* (2013.01);
(Continued)

(58) Field of Classification Search
None
See application file for complete search history.

(56) References Cited

U.S. PATENT DOCUMENTS

| 5,659,102 A | * | 8/1997 | Triantafillou ............. C07C 1/20 |
| | | | 585/639 |
| 6,004,527 A | | 12/1999 | Murrell et al. |

(Continued)

FOREIGN PATENT DOCUMENTS

| EP | 2070894 A1 | 6/2009 |
| EP | 2070896 A1 | 6/2009 |

(Continued)

OTHER PUBLICATIONS

Robin Smith, Reaction, Separation and Recycle Systems for Continuous Processes, Chemical Process Design and Integration, Wiley, 2005, p. 259-261.*

(Continued)

*Primary Examiner* — Philip Louie
(74) *Attorney, Agent, or Firm* — Osha Liang LLP

(57) ABSTRACT

A process for the production of jet and other heavy fuels from alcohols and mixture of alcohols is disclosed. The process may include contacting in a reaction zone at least one C2 to C11 alcohol with a solid catalyst having activity for the simultaneous dehydration of the alcohols to form olefins, isomerization of the olefins to form internal olefins, and oligomerization of the olefins produced in situ via the dehydration reaction to form an effluent comprising monoolefinic hydrocarbons. Preferably, the alcohol feed is a mixture of alcohols, such as C2 to C7 alcohols or C4 and C6 alcohols, enabling the production of a mixture of branched hydrocarbons that may be used directly as a jet fuel without blending.

28 Claims, 5 Drawing Sheets

(51) Int. Cl.
  *C07C 5/13* (2006.01)
  *C10G 45/58* (2006.01)
  *C10G 50/00* (2006.01)
  *C10G 69/12* (2006.01)
  *C10L 1/08* (2006.01)
  *C10G 3/00* (2006.01)

(52) U.S. Cl.
  CPC ............... *C10G 3/49* (2013.01); *C10G 45/58* (2013.01); *C10G 50/00* (2013.01); *C10G 69/126* (2013.01); *C10L 1/08* (2013.01); *Y02P 30/20* (2015.11)

(56) References Cited

U.S. PATENT DOCUMENTS

| | | | |
|---|---|---|---|
| 6,350,429 B1 | 2/2002 | Murrell et al. | |
| 6,809,055 B2 | 10/2004 | Overbeek et al. | |
| 6,936,742 B2 | 8/2005 | Smith, Jr. | |
| 7,084,087 B2 | 8/2006 | Shan et al. | |
| 7,098,161 B2 | 8/2006 | Yeh et al. | |
| 7,414,164 B2 | 8/2008 | Zak | |
| 7,470,645 B2 | 12/2008 | Shan et al. | |
| 7,501,548 B2 | 3/2009 | Brown et al. | |
| 7,510,644 B2 | 3/2009 | Overbeek et al. | |
| 7,550,405 B2 | 6/2009 | Shan et al. | |
| 7,559,961 B2 | 7/2009 | Jimeson et al. | |
| 7,737,315 B2 | 6/2010 | Brown et al. | |
| 8,232,440 B2 | 7/2012 | Holtzapple et al. | |
| 2003/0009070 A1* | 1/2003 | Doll | C07C 5/2518 585/664 |
| 2005/0112739 A1 | 5/2005 | Golubkov | |
| 2007/0092957 A1 | 4/2007 | Donaldson et al. | |
| 2008/0009656 A1 | 1/2008 | D'Amore et al. | |
| 2008/0013274 A1 | 1/2008 | Jobs et al. | |
| 2008/0015395 A1 | 1/2008 | D'amore et al. | |
| 2008/0015397 A1 | 1/2008 | D'Amore et al. | |
| 2008/0045754 A1 | 2/2008 | D'Amore et al. | |
| 2008/0131948 A1 | 6/2008 | Manzer et al. | |
| 2008/0220488 A1 | 9/2008 | D'Amore et al. | |
| 2008/0234523 A1 | 9/2008 | Manzer et al. | |
| 2009/0030239 A1 | 1/2009 | D'Amore et al. | |
| 2009/0099401 A1 | 4/2009 | D'Amore et al. | |
| 2009/0299109 A1* | 12/2009 | Gruber | C10L 1/04 585/14 |
| 2011/0288352 A1* | 11/2011 | Peters | C10G 3/42 585/14 |
| 2012/0271085 A1 | 10/2012 | Nesterenko et al. | |

FOREIGN PATENT DOCUMENTS

| | | |
|---|---|---|
| WO | 2009079213 A2 | 6/2009 |
| WO | 2011085223 A1 | 7/2011 |

OTHER PUBLICATIONS

Zeolyst International, Zeolite Beta, http://www.zeolyst.com/our-products/standard-zeolite-powders/zeolite-beta.aspx. Accessed May 22, 2017, p. 1.*

Correspondence reporting a First Office Action dated Mar. 23, 2015 in corresponding Chinese application No. (8 pages) 201310489583.4.

* cited by examiner

CONVERSION OF ALCOHOLS TO DISTILLATE FUELS

CROSS-REFERENCE TO RELATED APPLICATIONS

This application, pursuant to 35 U.S.C. § 119(e), claims priority to U.S. Provisional Application Ser. No. 61/716,120, filed Oct. 19, 2012, which is herein incorporated by reference in its entirety.

FIELD OF THE DISCLOSURE

Embodiments disclosed herein relate generally to a process for the production of jet and distillate fuels. More specifically, embodiments disclosed herein relate to processes for the conversion of C2 to C11 alkanols, including secondary alcohols, and mixtures or subsets thereof, to form jet and other heavy fuels.

BACKGROUND

Fermentation of sugars and starches derived from corn and other farm products has been widely used to produce ethanol, and today in the United States, ethanol is the largest biofuel used in the transportation fuels markets. There are many technologies that produce biofuels from biomass. For example, ethanol may be produced from lignocellulosic biomass. Isobutanol, as another example, can be formed from the fermentation of sugars which can be formed via the breakdown of cellulose. For example, solutions of up to approximately 2% by weight isobutanol in microbial growth have been produced in certain fermentation processes (Frances Arnold, "The Race for New Biofuels," Engineering & Science, No. 2, 2008). U.S. Patent Application Publication No. 20070092957 describes fermentatively producing isobutanol using recombinant microorganisms.

Nevertheless, there has been much research in alcohol fermentation technologies aimed at producing higher alcohols, such as C4 and C6 alcohols, which are more compatible with petroleum gasoline than ethanol, especially with regard to reduced water solubilities, decreased phase separations, and enhanced volumetric heating values. Technologies are also being developed for the production of mixed alcohols, such as C2 to C7 alcohols.

As microbes are further developed to withstand higher concentrations of alcohol, it can be envisioned that isobutanol may compete with ethanol as a potential fuel component or chemical feedstock derived from renewable resources. Unfortunately, there exist concerns regarding direct blending of isobutanol and other higher alcohols into the gasoline pool due to odor and automotive component compatibility issues. For this reason, there is interest in conversion of light alcohols into feedstocks for conversion into fuels, petrochemicals, or other valuable end products.

U.S. Patent Application Publication Nos. 20090099401, 20090030239, 2008013274, 20080045754, 20080015395, 20080234523, and others, each filed by E.I. Dupont de Nemours and Company, Wilmington, Del., are directed to the conversion of bio-derived isobutanol to butenes and isooctenes, among other end products. Each of these processes react isobutanol over a homogeneous or heterogeneous acid catalyst to form the desired reaction product, either a butene or an isooctene (diisobutylene).

Unlike tertiary butanol, which can be readily converted via dehydration into its constituent isobutylene and then into fuel blend components, such as diisobutylene, as disclosed in U.S. Pat. No. 6,936,742, the conversion of other light alcohols often requires higher activity catalysts and more severe process conditions. Significant recycle rates may also be required to result in acceptable conversion levels. Additionally, with bio-derived alcohols, water may be present with the feed, and separation is often difficult due to the components having closer relative volatilities and potential for forming various azeotropes.

U.S. Patent Application Publication No. 20050112739 discloses several process schemes for the conversion of C3-C5 alcohols from biomass fermentation to form fuel components. In a typical process, the C3-C5 alcohols separated from a fermentation broth are first dehydrated to C3-C5 olefins, which are then hydroformylated with biomass-derived synthesis gas to produce C4-C6 aldehydes. The C4-C6 aldehydes are then condensed over base catalysts into unsaturated C8-C12 iso-aldehydes that are then hydrogenated to saturated C8-C12 iso-alcohols. The thus obtained iso-alcohols are then dehydrated to their corresponding iso-olefins which are subsequently hydrogenated to a mixture of C8-C12 paraffins.

U.S. Pat. No. 8,232,440 also discloses several process schemes for conversion of alcohols to fuel components. Biomass is converted to a carboxylic acid, which is then reacted with an olefin to produce an ester. The ester is then hydrogenolyzed to produce alcohol, which may be converted via an oligomerization process, for example, to produce hydrocarbon. Other patents related to use of or conversion of alcohols to fuels may include U.S. Pat. Nos. 7,737,315, 7,501,548, 7,414,164, and 7,559,961.

SUMMARY OF THE CLAIMED EMBODIMENTS

In one aspect, embodiments disclosed herein relate to a process for the production of distillate fuels. The process may include: contacting in a reaction zone an alcohol or a mixture of two or more C2 to C11 alcohols, including at least one secondary alcohol, with a solid catalyst to form an effluent comprising mono-olefinic hydrocarbon oligomers. The solid catalyst may have activity for the simultaneous: dehydration of the alcohols to form olefins and water; oligomerization of the olefins produced in situ via the dehydration reaction; and isomerization of the resulting olefinic oligomers and olefins to form internal olefins.

In another aspect, embodiments disclosed herein relate to a process for the production of distillate fuels. The process may include: reacting an alcohol or a mixed alcohol feedstock in a first reaction zone and a second reaction zone to form an effluent comprising paraffinic hydrocarbons. The first reaction zone may include a first catalyst bed containing a catalyst having activity for the simultaneous dehydration of alcohols to olefins, isomerization of the olefins to form internal olefins, and oligomerization of the olefins produced in situ to form a mono-olefinic hydrocarbon product. The second reaction zone may comprise a second catalyst bed containing a catalyst having activity for the hydrogenation of the mono-olefinic hydrocarbon product. If necessary, water may be separated from the reaction products intermediate the first and second reaction zones.

Other aspects and advantages will be apparent from the following description and the appended claims.

DETAILED DESCRIPTION

Figure 1:
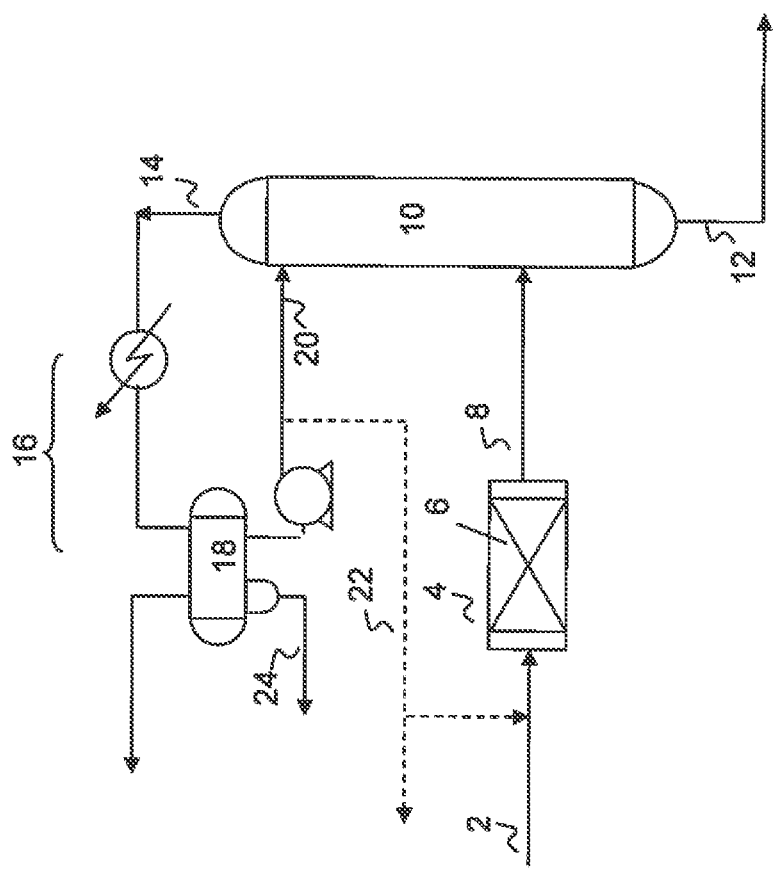
FIG. 1 is a simplified process flow diagram of a process for the production of distillate fuels according to embodiments disclosed herein.

Distillate fuels, as used herein, may include gas oils, diesel, kerosene, and jet fuels. Jet fuel is used herein to refer to a hydrocarbon mixture, for use in aviation turbine power unites, for example, that has a distillation end point (ASTM D-86 or similar) of about 250° C. In comparison, motor gasoline typically has a distillation end point of no higher than about 215° C. While some overlap in boiling ranges of motor gasoline and jet fuels exists, the fuels are distinguishable based on freezing points, allowable aromatics content, and other properties and specifications.

Reactors useful in embodiments disclosed herein may include traditional fixed bed reactors, boiling point reactors, and pulsed flow reactors, where the reactant flow and product flow may be co-current or counter-current. Boiling point and pulsed flow reactors may also provide for a continuous washing of the catalyst in addition to capturing at least a portion of the heat of reaction through evaporation, allowing for an improved reactor temperature profile as compared to conventional fixed bed reactors. Reactors useful in embodiments disclosed herein may be used as a stand-alone reactor or may be used in combination with one or more reactors of the same or different type.

Any type of reactor may be used to carry out the reactions described herein. The examples of reactors suitable for carrying out the reactions of embodiments herein may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, conventional fixed bed reactors, or any combination of these reactors. Multiple-reactor systems useful in embodiments disclosed herein may include a series of the same type of reactor or reactors in parallel, or different types of reactors in series, for the respective reaction zones. A person of ordinary skill in the art would recognize that other types of reactors may also be used.

In one aspect, embodiments herein relate to processes for the production of jet and other distillate or heavy fuels from an alcohol or a mixture of alcohols, such as C2-C11 primary alcohols (n-alcohols and iso-alcohols, such as n-butanol and iso-butanol), and secondary alcohols (such as 2-butanol). In some embodiments, the alcohol feed may include two or more C2-C11 alcohols, fed separately or as a mixture, and including at least one secondary alcohol. Secondary alcohols useful in embodiments disclosed herein may include 2-butanol, 2-pentanol, 3-pentanol, 2-hexanol, and 3-hexanol, among other alcohols where the OH group is in the 2-, 3-, 4-, or 5-position, etc. These secondary alcohols may be used alone, in mixtures, such as a mixture of C4 and C6 alcohols, or in combination with other C2-C11 alcohols such as ethanol, propanol, isopropanol, 1-butanol, isobutanol, and others, to form olefins, isoolefins and oligomers (dimers, trimers, etc.) of the olefins and isoolefins.

Production of fuels according to embodiments disclosed herein may be accomplished via the concurrent dehydration, oligomerization, and isomerization of the alcohols. Alkenes may be prepared by the dehydration of secondary alcohols. Concurrent with the dehydration reaction, the olefins may be isomerized to produce internal olefins and oligomerized (dimerization, trimerization, etc.) to form olefinic oligomers useful as distillate fuels, such as jet and other heavy fuels. Solid acid catalysts useful in embodiments disclosed herein and described further below thus include activity for the simultaneous dehydration of the alcohols to form olefins and water, isomerization of the olefins to form internal olefins, and oligomerization of the resultant olefins produced in situ. Side reactions may include the formation of dialkyl ethers, higher molecular weight oligomers and ethers, aromatics, and coke, which typically cause fouling of the catalyst.

Use of the respective alcohols or mixtures of alcohols may depend on the method of alcohol production/purification, selectivity of the catalyst to produce the desired alkene and the respective oligomers, the concentration of the higher alcohol, the resulting boiling point of the dialkyl ether, and the potential for the reactants and/or products to form an azeotrope with water, among other factors. For ease of separations, and to obtain substantially pure product streams, the boiling point of resulting oligomers (dimers, trimers, etc.) should be greater than the boiling point of water and the feed alcohol(s) under fractionation column or catalytic distillation reactor system operating conditions.

It has been surprisingly found that use of mixed alcohols, such as a mixture of C2 to C11 alcohols or various subsets thereof, such as a mixture of C4 and C6 alcohols, where the mixture includes at least one secondary alcohol, may result in the production of a mixture of branched paraffins that may be directly used as a distillate fuel, such as a diesel or jet fuel, without the need for blending. To achieve the desired branching, it is preferable to use alcohols that will form internal olefins upon dehydration, such as n-alcohols having the hydroxyl group in the 2-, 3-, 4-, or 5-position, etc. As alcohol sources and traditional fuel blendstocks may not be proximately located, the ability for production of a fuel grade product, without the need for blending, is clearly advantageous. Thus, embodiments disclosed herein may advantageously meet the stringent specifications for jet fuels; in comparison, prior art processes utilizing iso-alcohols cannot meet such requirements without significant blending.

In some embodiments, the alcohols useful in embodiments disclosed herein may include bio-alcohols, such as bio-derived 2-butanol, for example. Bio-alcohols are a feed material that may be derived from renewable resources, such as corn, corn stalks, corn cobs, lignocellulose, sugarcane, sugar beets, and wheat, among others. While direct blending of the alcohol into gasoline may be performed by simple mixing, the odor, vapor pressure, or material compatibility of the gasoline may be negatively affected due to the alcohol. Use of bio-alcohols according to embodiments disclosed herein may provide an alternative method to incorporate a renewable resource, bio-alcohol, as a gasoline feed stock, without the undesirable effects. In some embodiments, the bio-alcohols may be produced via fermentation. In other embodiments, the bio-alcohols may be produced via a process including biomass gasification to syngas followed by a modified Fischer-Tropsch synthesis.

Alcohol feeds useful in embodiments disclosed herein may contain impurities, such as water. For example, alcohols may contain a certain amount of water. Typically, the water is removed from the alcohol. However, as water is a byproduct of the alcohol dehydration reaction, alcohol feeds used in embodiments disclosed herein may include water as an impurity. Excessive water in the feed may decrease reactor conversion equilibrium, discussed below, and may result in increased reboiler duties, but water as a feed impurity may be tolerated in systems described herein.

In some embodiments, alcohol feeds may include up to 40 weight percent water; up to 30 weight percent water in other embodiments; up to 20 weight percent water in other embodiments; up to 10 weight percent water in other embodiments; up to 5 weight percent water in other embodiments; and up to 2 weight percent water in yet other embodiments. In other embodiments, alcohol feeds may be substantially pure alcohol or alcohol mixtures. In other embodiments, alcohol feedstocks useful in embodiments disclosed herein may contain from 0.1 to 100 wt. % alcohol and from 0 to 99.9 wt. % water. In other embodiments, the alcohol feedstock may contain from 10 to 100 wt. % alcohol; from 25 to 100 wt. % alcohol in other embodiments; and from 50 to 95 wt. % alcohol in yet other embodiments. The amount of water that may be used within the catalytic reaction zones may depend on (1) the reaction equilibrium constant and (2) the strength/activity of the acid catalyst for conversion. For example, as one moves from resin type catalysts to stronger sulfuric or hydrochloric acid concentrations, activity can be maintained at higher water concentrations. Acid resin catalysts will be more susceptible to loss in catalyst activity as one moves to larger quantities of water at elevated temperatures.

As described above, alcohols may be fed to a reactor system, where the alcohols contact a catalyst and react to form alkenes and water, and the in situ formed alkenes are isomerized to form internal olefins and reacted to form oligomers (preferably trimers or other hydrocarbons boiling in the jet or diesel fuel range) of the alkenes and/or isoalkenes. The oligomers, boiling at a temperature higher than water, may concurrently or subsequently be separated, such as recovering the oligomers as a bottoms fraction from a catalytic distillation reactor system or from a downstream distillation system. Water and the alkenes or isoalkenes may be recovered as an overhead fraction.

Referring now to FIG. 1, a simplified process flow diagram of a process for producing distillate fuels according to embodiments disclosed herein is illustrated. One skilled in the art would recognize that, although not depicted, pumps, valves, vessels, storage tanks, and other equipment commonly used for the processes described and illustrated herein are not shown so as to simplify the diagram.

An alcohol feedstock may be fed via flow line 2 to a reaction zone 4, such as a fixed bed reactor containing a bed 6 of a solid catalyst having activity for the simultaneous dehydration of the alcohols to form olefins, isomerization of the olefins to form internal olefins, and oligomerization of the mixture of olefins produced in situ via the dehydration and isomerization reactions to form an effluent comprising mono-olefinic hydrocarbons. The effluent from the reactor may be recovered via flow line 8, including the desired mono-olefinic oligomers, water from the dehydration reaction, unreacted alcohols, and any reaction byproducts, as noted above.

The effluent may then be fed via flow line 8 to separation system 10, such as a fractionation column, for separation of the oligomers from water and any unreacted alcohols, if any. The oligomers may be recovered as a bottoms fraction via flow line 12, and the water and unreacted alcohols may be recovered as an overheads fraction 14.

The water and at least a portion of the unreacted alcohols and other hydrocarbons in the overheads fraction may be condensed in an overheads recovery system 16 and the water and hydrocarbons may then be separated in a liquid/liquid separator 18. The liquid hydrocarbons recovered may be fed via flow line 20 as reflux for the column, may be recycled via flow line 22 for further contact with the catalyst to produce additional oligomers, and/or may be used for production of fuel range products as described below. The water may be withdrawn from the separator via flow line 24 and treated for disposal or use in other processes as known in the art.

Figure 2:
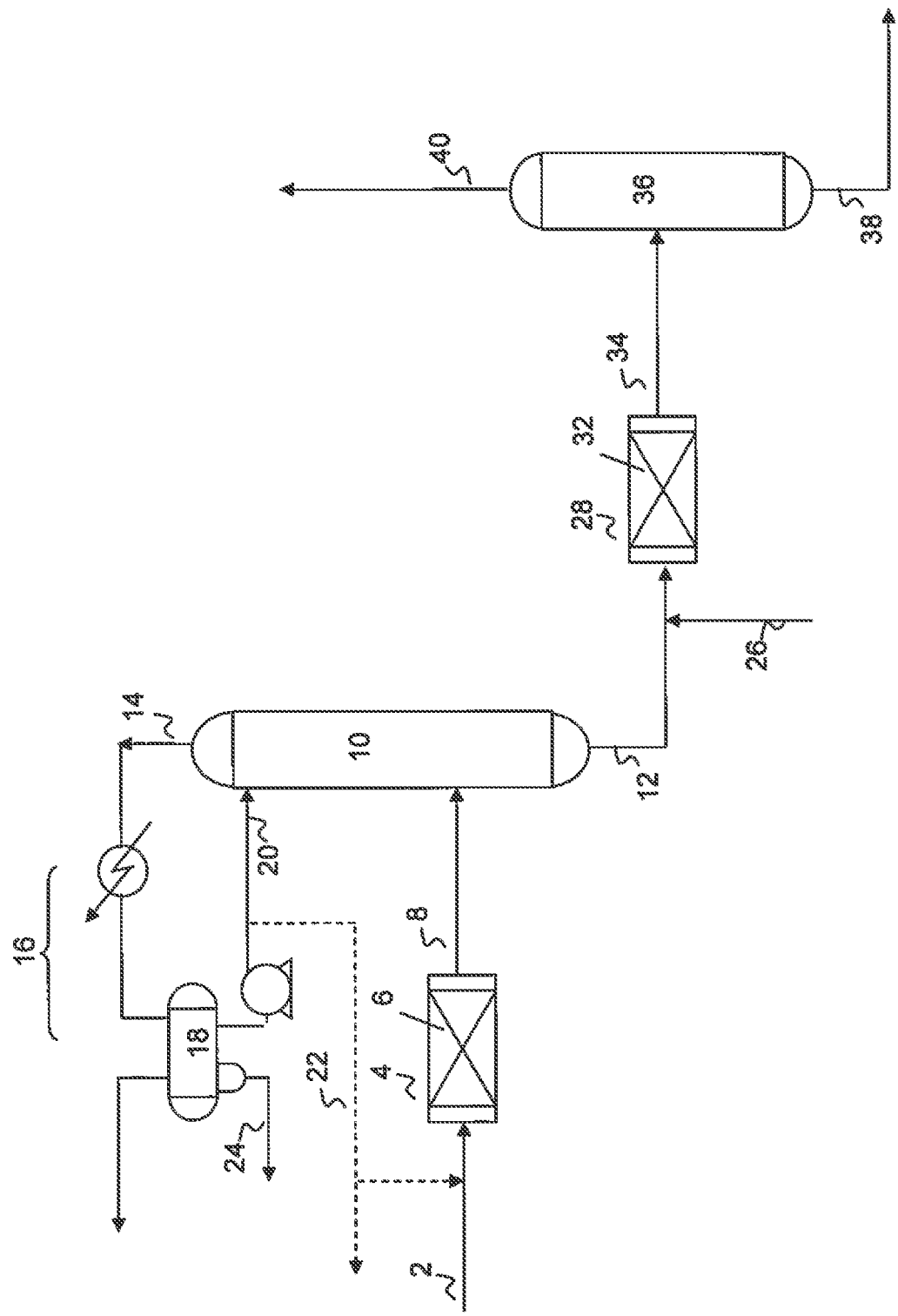
FIG. 2 is a simplified process flow diagram of a process for the production of distillate fuels according to embodiments disclosed herein.

Referring now to FIG. 2, a simplified process flow diagram of a system for the production of jet or other heavy fuels from alcohols according to embodiments disclosed herein is illustrated, where like numerals represent like parts. In this embodiment, the mono-olefinic oligomers formed via dehydration, isomerization, and oligomerization in reaction zone 4 and recovered as bottoms fraction 12 may be fed along with hydrogen, introduced via flow line 26, to hydrogenation reaction zone 28, such as a fixed bed reactor containing a bed 32 of hydrogenation catalyst. The hydrogen and the mono-olefinic hydrocarbons may then be reacted over the catalyst at appropriate conditions to form an effluent 34 comprising paraffinic hydrocarbons.

While the extent of oligomerization may be controlled to some degree by the operating conditions in reaction zone 4, a range of oligomers may be produced. The size and range of the oligomers produced may also depend on the alcohol feedstock used, where a mixed alcohol feed may form a broader range of products. As such, following hydrogenation it may be desirable to feed effluent 34 to a separation zone 36 for fractionation of the paraffinic hydrocarbons into two or more fractions 38, 40 useful as a fuel or a fuel blendstock. For example, where a mixture C4 and C6 secondary alcohols is used as a feedstock, the mono-olefinic hydrocarbons recovered from separation zone 10 via line 12 may include C8 (C4 dimer), C10 (mixed C4/C6 oligomer), C12 (C4 trimer, C6 dimer), C14 (mixed C4/C6 oligomer), C16 (mixed C4/C6 oligomer or C4 quadrimer), and C18 (C6 trimer or mixed C4/C6 oligomer), among other compounds. The C8 and C10 compounds may be useful as a gasoline blendstock, C10+ or C11+ compounds, or fractions thereof, may be useful as a diesel fuel, jet fuel, or other heavy distillate fuels or fuel blendstocks.

Figure 3:
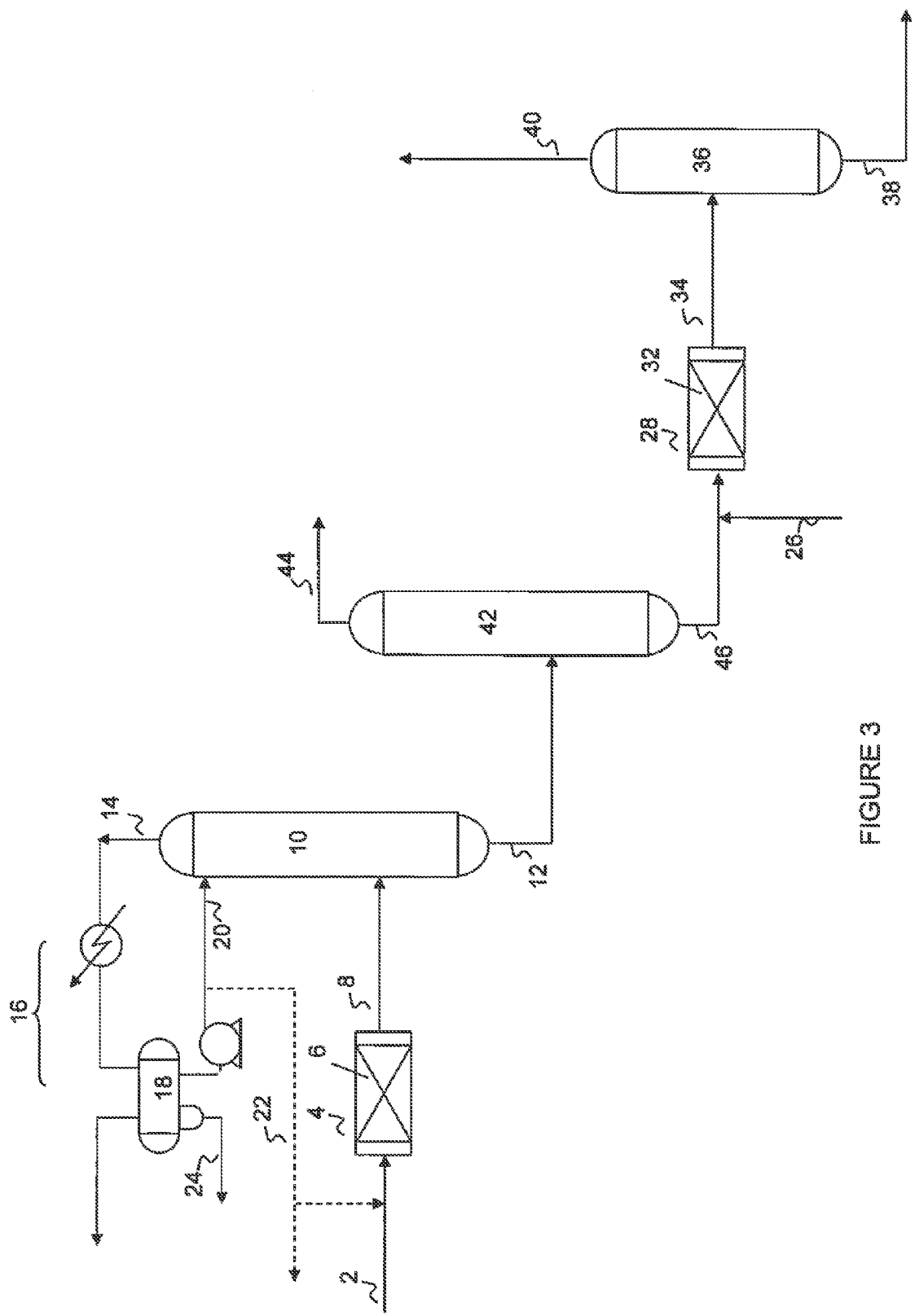
FIG. 3 is a simplified process flow diagram of a process for the production of distillate fuels according to embodiments disclosed herein.

Referring now to FIG. 3, a simplified process flow diagram of a system for the production of jet or other heavy fuels from alcohols according to embodiments disclosed herein is illustrated, where like numerals represent like parts. In this embodiment, the mono-olefinic oligomers formed via dehydration, isomerization, and oligomerization in reaction zone 4 and recovered as bottoms fraction 12 may be fractionated in a separation zone 42 to produce, for example, an overhead fraction 44 comprising C10 and lighter olefins and a bottoms fraction 46 comprising C11+ olefins. The C11+ bottoms fraction 46 may then be hydrogenated and further processed as described above. If desired, at least a portion of the C10 and lighter olefins in overheads 44 may be recycled (not shown) to reaction zone 4 for reaction with in situ produced olefins and oligomers to convert the C10 and lighter olefins to the more desirable heavy olefins.

Still referring to FIG. 3, in other embodiments, it may be desirable to produce a greater amount of jet range products, and limiting the amount of C12 and lighter products. In such embodiments, the mono-olefinic oligomers formed via dehydration, isomerization, and oligomerization in reaction zone 4 and recovered as effluent 8 may be fractionated in separation zone 10 and/or separation zone 42, which may include one or more distillation columns, to produce, for example, overhead fraction(s) 14, 44 comprising C12 and lighter olefins and bottoms fraction(s) 46 comprising C13+ olefins. The C13+ bottoms fraction 46 may then be hydrogenated and further processed as described above. If desired, at least a portion of the C12 and lighter olefins in overheads 14, 44 may be recycled (such as via line 22; not shown from line 44) to reaction zone 4 for reaction with in situ produced olefins and oligomers to convert the C12 and lighter olefins to the more desirable heavy olefins in the jet fuel range.

For example, separation zone 10 may be operated to include C6 or C8 compounds in the overheads, for use as reflux and recycle. Separation zone 42 may then be used to separate C10 and C12 components, recovered in overheads 44, from C13+ hydrocarbons, recovered in bottoms 46.

Figure 4:
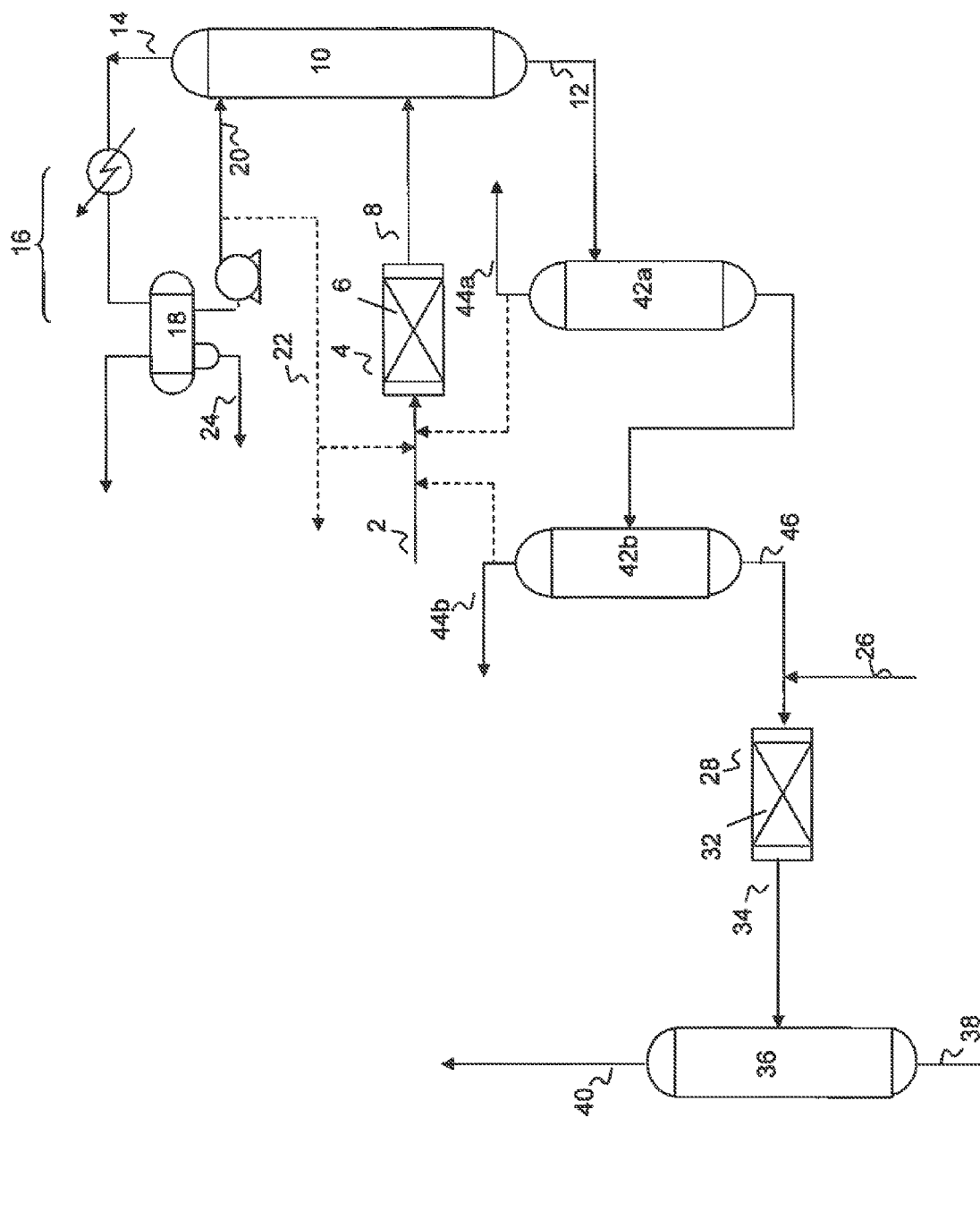
FIG. 4 is a simplified process flow diagram of a process for the production of distillate fuels according to embodiments disclosed herein.

Alternatively, such as illustrated in FIG. 4, multiple distillation columns 42 (42a, 42b) may be used to separate the oligomers into desired fractions. Column 42a may be used, for example, to separate C8 and lighter olefins, recovered as overheads fraction 44a, the whole or a portion of which may be recycled to reactor 4. Column 42b may be used, for example, to separate C12 and lighter olefins, recovered as overheads 44b, the whole or a portion of which may be recycled to reactor 4. Column 36 may then be used to separate the C13+ hydrocarbons into desired fractions. In this manner, the process may include product flexibility, allowing for production of numerous fractions, with the ability to control the ratio of gasoline range hydrocarbons, diesel range hydrocarbons, and jet range hydrocarbons, among others, based on the fractionation conditions (hydrocarbon ranges recovered in the various streams), and the proportion recycled for continued reaction or recovered as a product.

In various embodiments, heat transfer systems may be used to integrate the heating and cooling of the feed and product streams. For example, the alcohol feed may be heated using at least a portion of the overhead stream, at least a portion of the bottoms stream, or a combination thereof. Other heat integration configurations may also be used.

Catalysts useful in the dehydration/isomerization/oligomerization reaction, as mentioned above, include various acidic catalysts. Alcohol dehydration and isoolefin oligomerization, for example, is a catalytic reaction that may be performed using an acid resin catalyst. Catalysts useful in the dehydration/isomerization/oligomerization reaction may also include natural and synthetic zeolites and metal substituted cationic resin catalysts, but other acidic or mildly acidic catalyst may also be used, including phosphoric acid treated clays.

Catalysts used in the fixed bed dehydration/isomerization/oligomerization reactor in various embodiments disclosed herein may include metal-treated zeolites, either acidic or basic, hydrofluoric acid-treated clays, and silica-alumina catalysts, such as a 20% silica-alumina, among the other catalysts described above.

In some embodiments, the catalysts used in the dehydration/isomerization/oligomerization reaction zones include one or more of: an acidic zeolite with a SAR from about 10 to about 100; a steamed or metal ion exchanged zeolite; mesoporous aluminosilicates or zirconiasilicates; sulphated or phosphated mesoporous aluminosilicates or zirconiasilicates; metal cation exchanges resins and AMBERLYSTs, and DOWEXs; and zeolite-mesoporoous silica composites.

In some embodiments, the catalysts used in the dehydration/isomerization/oligomerization reaction zones include one or more beta zeolite-containing catalysts. For example, in some embodiments, the beta zeolite-containing catalyst may include one or more of the catalysts disclosed in U.S. Pat. No. 6,004,527, U.S. Pat. No. 6,350,429, U.S. Pat. No. 6,809,055, U.S. Pat. No. 7,084,087, U.S. Pat. No. 7,098,161, U.S. Pat. No. 7,470,645, U.S. Pat. No. 7,510,644, and U.S. Pat. No. 7,550,405, each of which being incorporated herein by reference, among others.

Operating conditions in the fixed bed dehydration/isomerization/oligomerization reactor may depend upon the purity of the alcohol feed, the particular alcohol(s) used, and the types of catalyst used, among other variables. Typical reaction zone operating conditions include temperatures ranging from 50° C. to 500° C. and pressures ranging from greater than 0 to 200 bar. In other embodiments, reaction zone operating conditions may include temperatures ranging from 100° C. to 300° C. and pressures ranging from greater than 0 to 1000 psig; and may include temperatures ranging from 110° C. to 500° C. and pressures ranging from greater than 0 to 200 bar in yet other embodiments.

In some embodiments, dehydration/isomerization/oligomerization reactor temperatures may range from about 100° C. to about 300° C. (about 212 to about 572° F.). In other embodiments, dehydration/oligomerization reactor temperatures may range from about 120° C. to about 260° C. (about 248 to about 500° F.); from about 150° C. to about 200° C. (about 302 to about 392° F.) in other embodiments; and from about 200° C. to about 240° C. (about 302 to about 464° F.), such as about 220° C. (about 428° F.), in yet other embodiments. In some embodiments, dehydration/isomerization/oligomerization reactor pressures may range from greater than 0 bar to about 200 bar (absolute). In other embodiments, dehydration/isomerization/oligomerization reactor pressures may range from about 1 bar to about 100 bar; from about 3 bar to about 50 bar in other embodiments; from about 5 bar to about 45 bar in other embodiments; and from about 20 to about 30 bar, such as about 25 bar, in yet other embodiments. The operating temperature and pressure selected may depend upon desired conversion and phase(s) of the reactants and products, among others.

The conditions used in the dehydration/isomerization/oligomerization reactor should be sufficient to dehydrate at least a portion of the alcohol. In other embodiments, more severe conditions may be used in the dehydration/isomerization/oligomerization reactor so as to dehydrate the alcohol and at least trimerize (or higher degrees of oligomerization) at least a portion of the resulting alkene.

The severity of operating conditions in the dehydration/isomerization/oligomerization reactor may also depend upon the amount of alcohol conversion required. The amount of alcohol conversion required may also affect the choice of catalyst used in the dehydration/isomerization/oligomerization reactor. For example, a desired dehydration/oligomerization reactor conversion of 20 weight percent may require less severe operating conditions and/or a lower activity catalyst than for a fixed bed dehydration/isomerization/oligomerization reactor conversion approaching equilibrium.

Catalysts useful in the hydrogenation reactor may include Group VIII metals, such as cobalt, nickel, palladium, or platinum, alone or in combination, and/or in combination with other metals, such as a Group V or Group VI metal, such as molybdenum or tungsten, on a suitable support, which may be alumina, silica, titania, silica-alumina, titania-alumina, titania-zirconia, or the like. Normally the catalytic metals are provided as the oxides of the metals supported on extrudates or spheres. Catalysts containing a Group VIB metal, such as molybdenum, and a Group VIII metal, such as cobalt or nickel, are preferred. Catalysts suitable for the hydrogenation reaction include palladium, platinum, cobalt-molybdenum, nickel-molybdenum and nickel-tungsten, among others. The metals may be reduced to the hydride form, sulfide form, or other active states, if necessary, prior to use by exposure to hydrogen, for example.

The hydrogenation catalyst typically is in the form of extrudates having a diameter of ⅛, 1/16 or 1/32 inches and an L/D of 1.5 to 10. The catalyst also may be in the form of spheres having similar diameters. They may be directly loaded into standard single pass fixed bed reactors which include supports and reactant distribution structures.

The catalyst and operating conditions in the hydrotreatment/hydrogenation reactor may depend upon the particular alcohol(s) used to produce the dimers and trimers, the particular flow scheme (with or without guard beds to remove acid throw from the trimerization catalyst), the desired conversion to trimer and dimer to paraffins, and the tolerance in end products for any isomerization that may occur under hydrogenation conditions, among other variables. Typical hydrogenation reaction zone operating conditions include temperatures in the range from 100° C. to 500° C. and pressures ranging from 1 to 100 bar.

In some embodiments, hydrogenation reactor temperatures may range from about 100° C. to about 300° C. (about 212 to about 572° F.). In other embodiments, hydrogenation reactor temperatures may range from about 120° C. to about 260° C. (about 248 to about 500° F.); from about 130° C. to about 180° C. (about 266 to about 356° F.) in other embodiments; and from about 140° C. to about 170° C. (about 284 to about 338° F.) in yet other embodiments. In some embodiments, hydrogenation reactor pressures may range from about 3 bar to about 200 bar (absolute). In other embodiments, hydrogenation reactor pressures may range from about 5 bar to about 100 bar; from about 10 bar to about 50 bar in other embodiments; from about 15 bar to about 45 bar in other embodiments; and from about 20 to about 30 bar, such as about 25 bar, in yet other embodiments. If necessary to control temperature across the hydrogenation reactor, recycle of paraffinic products may be used as a diluent, where a ratio of diluent to feed may be in the range from about 0.1:1 to about 10:1; in other embodiments, the recycle to feed ratio may be in the range from about 1:1 to about 5:1; from about 1.5:1 to about 3.5:1 in yet other embodiments.

As described above, the conversion of alcohols to distillate fuel range paraffins may take place in two or more reaction zones, one zone for dehydration/isomerization/oligomerization and a separate zone for hydrogenation of the olefinic oligomers to form paraffins. It may be desirable to limit the number of reactors and associated equipment so as to decrease capital costs associated with processes described herein.

Figure 5:
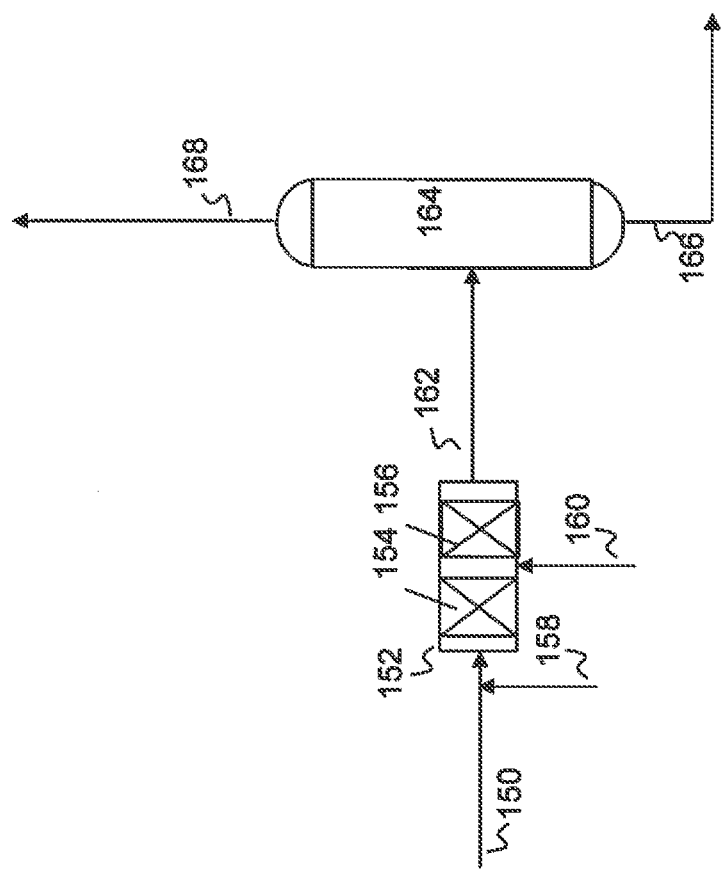
FIG. 5 is a simplified process flow diagram of a process for the production of distillate fuels according to embodiments disclosed herein.

Referring now to FIG. 5, a simplified flow diagram for processes for the production of distillate fuels having a reduced piece count according to embodiments disclosed herein are illustrated. In FIG. 5, an alcohol feedstock is fed via flow line 150 to a reaction zone 152 containing a first catalyst bed 154 and a second catalyst bed 156. The first catalyst bed 154 may contain a catalyst having activity for the simultaneous dehydration of alcohols to olefins, isomerization of the olefins to internal olefins, and for the oligomerization of the olefins produced in situ to form a mono-olefinic hydrocarbon products. The second catalyst bed 156 may contain a catalyst having activity for the hydrogenation of the mono-olefinic hydrocarbon oligomers produced in the first catalyst bed. Hydrogen may be fed via flow lines 158, 160 to the reaction zone along with the feed and/or upstream of the second catalyst bed for the hydrogenation reaction. Reaction of the alcohol or mixture of alcohols over the catalysts may thus form an effluent 162 comprising paraffinic hydrocarbons (the hydrogenated oligomers), water, and unreacted hydrogen and alcohols, if any. The effluent 162 may then be separated in separation zone 164 to recover the desired paraffinic products as a bottoms fraction 166 and water and any unreacted alcohols as an overheads fraction 168, which may be separated and used as described above (reflux, recycle or other options mentioned). In this embodiment, the hydrogenation catalyst should be alcohol- and water-tolerant, as unreacted alcohol may be present and water is produced as a reaction product over the dehydration catalyst.

EXAMPLES

Mixed Alcohol Feed to Jet

A reaction system similar to that as illustrated in FIG. 2, with olefins recycle to the oligomerization reactor, containing a beta zeolite-containing catalyst, was used to dehydrate and oligomerize a mixed alcohol feed system. The composition of the mixed alcohol feedstock is presented in Table 1.

TABLE 1

| Total Alcohol (wt %) | 88.6 |
| --- | --- |
| Water (wt %) | 2.74 |
| Amines, ketones, other oxygenates (wt %) | 8.66 |
| N (ppm) | 755 |
| S (ppm) | <1 |
| Alcohols C# Distribution | |
| C3 | 29.8 |
| C4 | 21.9 |
| C5 | 17.9 |
| C6 | 12.5 |
| C7 | 10.9 |
| C8-C12 | 7.0 |

A summary of the oligomerization reaction conditions and performance achieved over the test with the above mixed alcohol feed composition is provided in Table 2.

TABLE 2

| Alcohols Converstion per Pass (wt %) | 99+ |
| --- | --- |
| Recycle Olefins/Mixed Alcohol Feed (w/w ratio) | 1/1 |
| Average Net Jet Range Olefins Yield (on mixed alcohol feed) (liquid vol %) | 57.4 |
| Oligomerization Reactor Temeperature Range (° C.) | 250-290 |
| Oligomerization Reactor Pressure (psig) | 200 |
| Oligomerization WHSV (kg mixed alcohol/h/kg catalyst) | 0.25 |

The biojet samples were tested, and were found to meet the following ASTM specifications for jet fuels: Distillation D86, freeze point D2386, viscosity @−20° C. ASTM D445, Olefins by FIA D1319, and density @ 15° C. D4052.

The experiments performed indicated that the yield of jet fuel was impacted to an extent based on the distribution of alcohols in the feed mixture, among other factors.

IBA to Jet

A similar process flow scheme was used to determine the effectiveness of converting isobutanol (IBA) feedstocks to biojet fuels using a beta zeolite-containing catalyst. The tests were carried out with a fixed bed reactor in vapor phase at 250° C. to 275° C. temperature, 200-250 prig pressure, and 0.25 to 0.50 WHSV.

Single pass conversions of the alcohol were typically greater than 99 wt %, resulting in a biojet range olefins yield of 20 to 30 liquid vol % for once-through IBA only feed. Recycle of C8 olefins through the reactor (~0.7:1 octenes to alcohol, based on weight) increased the yield of jet, attaining in some runs 75 to 90% of the theoretical maximum jet range olefin yields.

As described above, alcohols or mixtures of alcohols, including secondary alcohols, may be used to produce distillate fuels, such as those boiling in the range of jet fuel. Depending upon the makeup of the resulting products, such distillate fuels may be used as a fuel or a fuel blendstock.

It has been surprisingly found, however, that use of mixed alcohols, such as a mixture of C2 to C11 alcohols or various subsets thereof, such as a mixture of C4 and C6 alcohols, and including at least one secondary alcohol, may result in the production of a mixture of branched paraffins that may be directly used as a jet or diesel fuel without the need for blending with petroleum-derived jet or diesel fuels. As alcohol sources and traditional fuel blendstocks may not be proximately located, the ability for production of a fuel grade product, without the need for blending or only a need for minimal blending, is clearly advantageous. The use of mixed alcohols may also facilitate cross-oligomerization, resulting in the production of a more jet fuel-like and petroleum-like product than prior art processes using a single alcohol feedstock, such as isobutanol, to produce one or two compounds that happen to boil in the jet fuel or distillate fuel range.

Other various embodiments as described above are not illustrated. However, one skilled in the art would readily be able to envision such flow schemes based upon the description and figures presented.

As described above, embodiments disclosed herein provide for the conversion of lower alcohols to form jet, diesel, and other distillate fuel-range products. While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of distillate fuel range hydrocarbons, the process comprising:
   contacting in a reaction zone a mixture of two or more C2 to C11 alcohols, including at least one secondary alcohol, with a solid acid catalyst, at conditions where the solid acid catalyst has activity for the simultaneous:
   i. dehydration of the alcohols to form olefins and water;
   ii. isomerization of the resulting olefins to form internal olefins; and
   iii. oligomerization of the olefins produced in situ;
   to form an effluent comprising mono-olefinic hydrocarbon oligomers including the distillate fuel range hydrocarbons;
   wherein the mixture of two or more C2 to C11 alcohols includes one or more C7 to C11 alcohols.

2. The process of claim 1, further comprising separating the mono-olefinic hydrocarbon oligomers from water, any unreacted alcohols, and any unreacted olefins.

3. The process of claim 2, further comprising recycling at least one of the unreacted alcohols and the unreacted olefins to the reaction zone.

4. The process of claim 1, further comprising hydrogenating the mono-olefinic hydrocarbon oligomers to produce a paraffinic hydrocarbon product.

5. The process of claim 4, further comprising fractionating the paraffinic hydrocarbon product into one or more hydrocarbon fractions useful as a fuel or a fuel blendstock.

6. The process of claim 5, wherein the one or more hydrocarbon fractions are suitable for use as a fuel grade product, without blending with petroleum-derived fuels.

7. The process of claim 1, wherein the C2 to C11 alcohols are provided from a biomass fermentation or a biomass gasification to syngas followed by a modified Fischer-Tropsch synthesis.

8. The process of claim 1, wherein the at least one secondary alcohol comprises at least one of 2-butanol, 2-pentanol, 2-hexanol, and combinations thereof.

9. The process of claim 1, wherein the mixture of two or more C2 to C11 alcohol comprises either a mixture of C4 and C6 alcohols or a mixture of C2 to C7 alcohols.

10. The process of claim 1, further comprising fractionating the mono-olefinic hydrocarbon oligomers to produce one or more fractions comprising C10 or C12 and lighter olefins and one or more fractions comprising C11+ or C13+ olefins, respectively.

11. The process of claim 10, further comprising recycling at least a portion of the one or more fractions comprising C10 or C12 and lighter olefins to the reaction zone for reaction with in situ produced olefins and oligomers.

12. The process of claim 1, wherein the solid acid catalyst is a beta zeolite-containing catalyst.

13. A process for the production of distillate fuel range hydrocarbons, the process comprising:
   reacting an alcohol feedstock in a first reaction zone and a second reaction zone, the first reaction zone comprising a first catalyst bed containing an acid catalyst and operated at conditions where the acid catalyst has activity for the simultaneous dehydration of alcohols to olefins, isomerization of the olefins to form internal olefins, and oligomerization of the olefins produced in situ to form a mono-olefinic hydrocarbon product, and the second reaction zone comprising a second catalyst bed containing a catalyst having activity for the hydrogenation of the mono-olefinic hydrocarbon product to form an effluent comprising paraffinic hydrocarbons, including the distillate fuel range hydrocarbons;
   wherein the alcohol feedstock comprises a mixture of two or more C2 to C11 alcohols, and wherein one or more of the C2 to C11 alcohols are C7 to C11 alcohols.

14. The process of claim 13, wherein the acid catalyst is a beta zeolite-containing catalyst.

15. The process of claim 13, further comprising separating the paraffinic hydrocarbons from unreacted alcohols.

16. The process of claim 13, further comprising fractionating the paraffinic hydrocarbons into one or more hydrocarbon fractions useful as a fuel or a fuel blendstock.

17. The process of claim 13, wherein the first and second reaction zones are contained in the same reaction vessel.

18. The process of claim 13, further comprising separating water and unreacted alcohols from the molo-olefinic hydrocarbon product intermediate the first reaction zone and the second reaction zone.

19. A process for the production of distillate fuel range hydrocarbons, the process comprising:

contacting in a reaction zone a mixture comprising a C4 alcohol and one or more C7 to C11 alcohols with a solid acid catalyst at operating conditions where the solid acid catalyst has activity for the simultaneous:
  i. dehydration of the alcohol to form olefins and water;
  ii. isomerization of the resulting olefins to form internal olefins; and
  iii. oligomerization of the olefins produced in situ;
to form an effluent comprising mono-olefinic hydrocarbon oligomers including the distillate fuel range hydrocarbons.

20. The process of claim 19, further comprising separating the mono-olefinic hydrocarbon oligomers from water, any unreacted alcohols, and any unreacted olefins.

21. The process of claim 20, further comprising recycling at least a portion of the unreacted alcohols to the contacting.

22. The process of claim 20, further comprising recycling at least a portion of the unreacted olefins to the reaction zone.

23. The process of claim 19, further comprising fractionating the mono-olefinic hydrocarbon oligomers to produce one or more fractions comprising C12 and lighter olefins and one or more fractions comprising C13+ olefins.

24. The process of claim 23, further comprising recycling at least a portion of the C12 and lighter olefins fraction(s) to the reaction zone for continued reaction with in situ produced olefins and oligomers.

25. The process of claim 19, further comprising fractionating the mono-olefinic hydrocarbons oligomers to produce a fraction including C8 and lighter olefinic oligomers, a fraction including C9 to C12 olefinic oligomers, and a fraction including C13+ oligomers.

26. The process of claim 25, further comprising recycling at least a portion of the fraction including C8 and lighter olefinic oligomers to the reaction zone.

27. The process of claim 25, further comprising recycling at least a portion of the fraction including C9 to C12 olefinic oligomers to the reaction zone.

28. The process of claim 19, wherein the C4 alcohol comprises at least one of n-butanol, isobutanol, and 2-butanol.

* * * * *